US010166083B2

(12) United States Patent
Paradis et al.

(10) Patent No.: US 10,166,083 B2
(45) Date of Patent: Jan. 1, 2019

(54) METHOD AND SYSTEM FOR TRACKING OBJECTS IN COMPUTER-ASSISTED SURGERY

(71) Applicant: ORTHOSOFT INC., Montreal (CA)

(72) Inventors: Francois Paradis, Boucherville (CA); Joel Zuhars, Warsaw, IN (US); Karine Duval, Montreal (CA); Mathieu Chevrier, Roxboro (CA)

(73) Assignee: ORTHOSOFT INC., Montreal (CA)

( * ) Notice: Subject to any disclaimer, the term of this patent is extended or adjusted under 35 U.S.C. 154(b) by 0 days.

(21) Appl. No.: 15/681,804

(22) Filed: Aug. 21, 2017

(65) Prior Publication Data
US 2018/0000554 A1 Jan. 4, 2018

Related U.S. Application Data

(63) Continuation of application No. 13/783,495, filed on Mar. 4, 2013, now Pat. No. 9,763,738.

(60) Provisional application No. 61/605,788, filed on Mar. 2, 2012.

(51) Int. Cl.
 A61B 34/20 (2016.01)
 A61B 90/14 (2016.01)
 A61F 2/46 (2006.01)
 A61F 2/34 (2006.01)
 A61B 90/00 (2016.01)

(52) U.S. Cl.
 CPC .............. *A61B 90/14* (2016.02); *A61B 34/20* (2016.02); *A61F 2/4609* (2013.01); *A61F 2/4657* (2013.01); *A61B 2034/2051* (2016.02); *A61B 2090/3983* (2016.02); *A61F 2/34* (2013.01); *A61F 2002/4632* (2013.01); *A61F 2002/4668* (2013.01)

(58) Field of Classification Search
 CPC ........ A61B 19/5244; A61B 2019/5426; A61B 2019/5248; A61B 2019/5251; A61B 2019/5454; A61B 2562/0223
 See application file for complete search history.

(56) References Cited

U.S. PATENT DOCUMENTS

| 6,214,019 | B1 | 4/2001 | Manwaring et al. |
| 8,241,296 | B2* | 8/2012 | Wasielewski .......... A61B 17/00 606/96 |
| 8,442,621 | B2 | 5/2013 | Gorek |
| 2009/0003975 | A1 | 1/2009 | Kuduvalli et al. |
| 2010/0036384 | A1 | 2/2010 | Gorek |

* cited by examiner

*Primary Examiner* — Anu Ramana
(74) *Attorney, Agent, or Firm* — Norton Rose Fulbright Canada LLP

(57) ABSTRACT

A computer-assisted surgery system comprises instruments adapted to be used to perform tasks related to surgery. A reference device is in a fixed relation to a bone. A rotating magnet creates a magnetic field plane, the rotating magnet being connected to one of the instrument and the reference device. A magnetometer on the other of the instrument and the reference device produces signals as a function of at least its orientation relative to the magnetic field plane. A processing unit tracks said orientation of the instrument relative to the bone using said signals from the magnetometer subjected to the magnetic field plane.

11 Claims, 6 Drawing Sheets

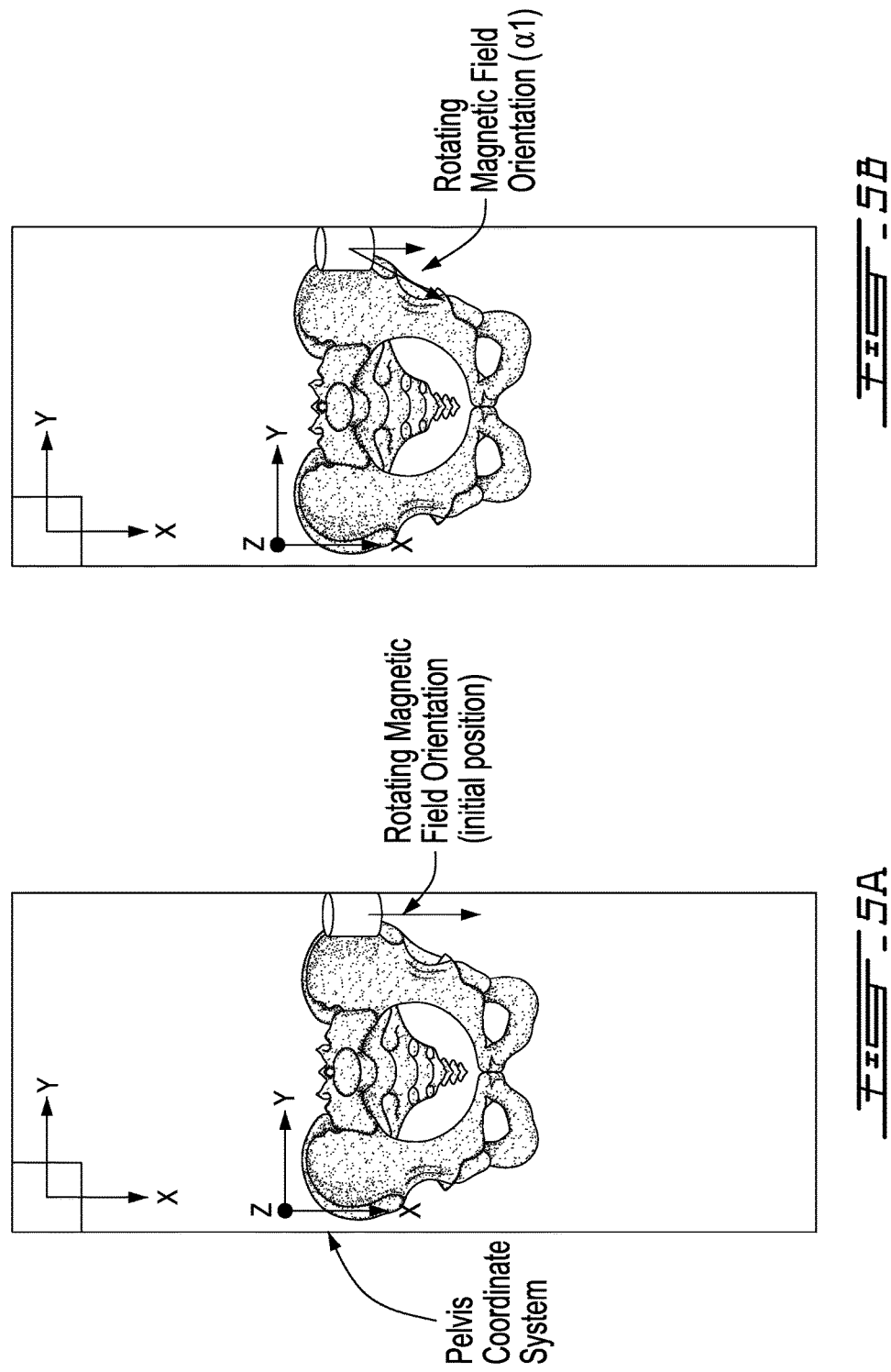

METHOD AND SYSTEM FOR TRACKING OBJECTS IN COMPUTER-ASSISTED SURGERY

CROSS-REFERENCE TO RELATED APPLICATION

The present application is a continuation of U.S. non-provisional patent application Ser. No. 13/783,495, now U.S. Pat. No. 9,763,738, filed on Mar. 4, 2013 which claims priority on U.S. Provisional Patent Application Ser. No. 61/605,788, filed on Mar. 2, 2012.

FIELD OF THE APPLICATION

The present application relates to orthopedic surgery using inertial sensors for navigation of surgical tools and instruments.

BACKGROUND OF THE ART

Inertial sensors (e.g., accelerometers, gyroscopes, inclinometers, etc.) are increasingly used in computer-assisted surgery for numerous reasons. Off-the-shelf inertial sensors are relatively inexpensive and may produce results of sufficient precision and accuracy for orthopedic surgery applications.

A common trait of inertial sensors is that they often do not provide positional information but, rather, simply orientational information, as they operate relative to gravity or by measuring accelerations. Therefore, methods must be devised to create bone references and tools using inertial sensors taking into consideration the absence of positional information.

SUMMARY OF THE APPLICATION

It is therefore an aim of the present invention to provide a novel CAS tracking system and method.

Therefore, in accordance with the present application, there is provided a computer-assisted surgery system comprising: at least one instrument adapted to be used to perform a task related to surgery; a reference device adapted to be in a fixed relation to a bone; a rotating magnet creating a magnetic field plane, the rotating magnet connected to one of the instrument and the reference device; a magnetometer on the other of the instrument and the reference device, the magnetometer producing signals as a function of at least its orientation relative to the magnetic field plane; and a processing unit for tracking said orientation of the instrument relative to the bone using said signals from the magnetometer subjected to the magnetic field plane.

BRIEF DESCRIPTION OF THE DRAWINGS

FIGS. 5A to 5D are schematic views of the method of FIG. 4 as used in pelvic surgery.

DESCRIPTION OF THE EXEMPLARY EMBODIMENTS

Figure 1:
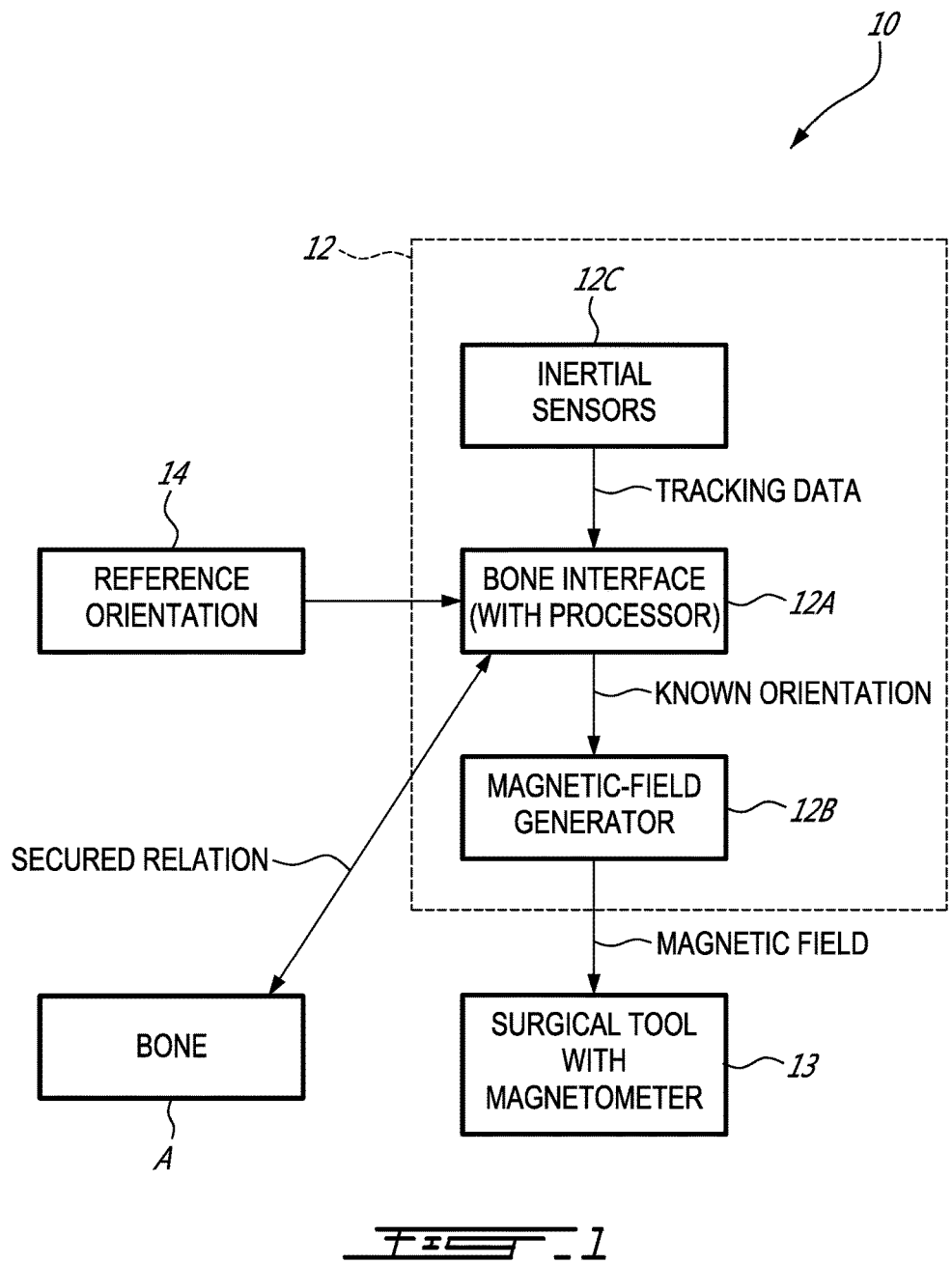
FIG. 1 is a block diagram of a magnetometer computer-assisted surgery (CAS) system in accordance with an embodiment of the present disclosure.

Referring to the drawings, and more particularly to FIG. 1, a magnetometer computer-assisted surgery (CAS) tracking system is generally shown at 10. The system 10 is used to guide an operator during the navigation of surgical tools by providing orientation-based information of surgical tools, such as anteversion and abduction/adduction angles, relative to a bone. For simplicity purposes, the CAS tracking system 10 is described in the following paragraphs as being used for acetabular surgery on the pelvis. However, any other appropriate type of orthopedic surgery could benefit from the use of the CAS tracking system 10 (e.g., knee, femur, shoulder, etc), provided the system 10 is configured for such procedures.

The system 10 comprises a pelvic reference 12 that is used as a frame of reference (i.e., coordinate system) for the tracking of objects relative to the bone (i.e., in the illustrated embodiment, the pelvis). The pelvic reference 12 comprises a bone interface 12A by which it is connected to a bone, or fixedly secured to be immovable relative to the bone, and a magnetic-field generator 12B, supported by the bone interface 12A and may also comprise tracking technology, such as an inertial sensor unit 12C. The pelvic reference 12 may also have an visual display interface as part of the bone interface 12A, to output and display tracking data in various forms, with a processor unit within the bone interface 12A or remote therefrom. The magnetic-field generator 12B will be used in combination with a surgical tool 13 featuring a magnetometer, or vice-versa (magnetometer on reference, and magnetic-field generator on the tool). The magnetometer will provide navigational data as a result of being exposed to the magnetic field created by the magnetic-field generator 12B.

A reference orientation 14 may be used in combination with the pelvic reference 12, to create the coordinate system of the pelvic reference 12 or calibrate the pelvis reference 12 for subsequent navigation. More specifically, the pelvic reference 12 may use the inertial sensor unit 12C, which must be calibrated relative to a bone to create a coordinate system, and the reference orientation 14 may be used for referencing purposes. The reference orientation 14 is a calibrated 3-axis orientation, and this calibration is transferred to a processor of the pelvic reference 12, with the output of the inertial sensor unit 12C affecting the 3-axis orientation. As an example, copending United States Application Publications No. US 2009/0247863 and, No. US 2009/0248044 pertain to the calibration of such reference orientation 14, and are incorporated herein by reference. Other calibration and/or referencing methods may also be used. For instance, the reference orientation 14 may comprise given tools, and/or steps of manipulations to determine the orientation of the pelvic reference 12.

Figure 2:
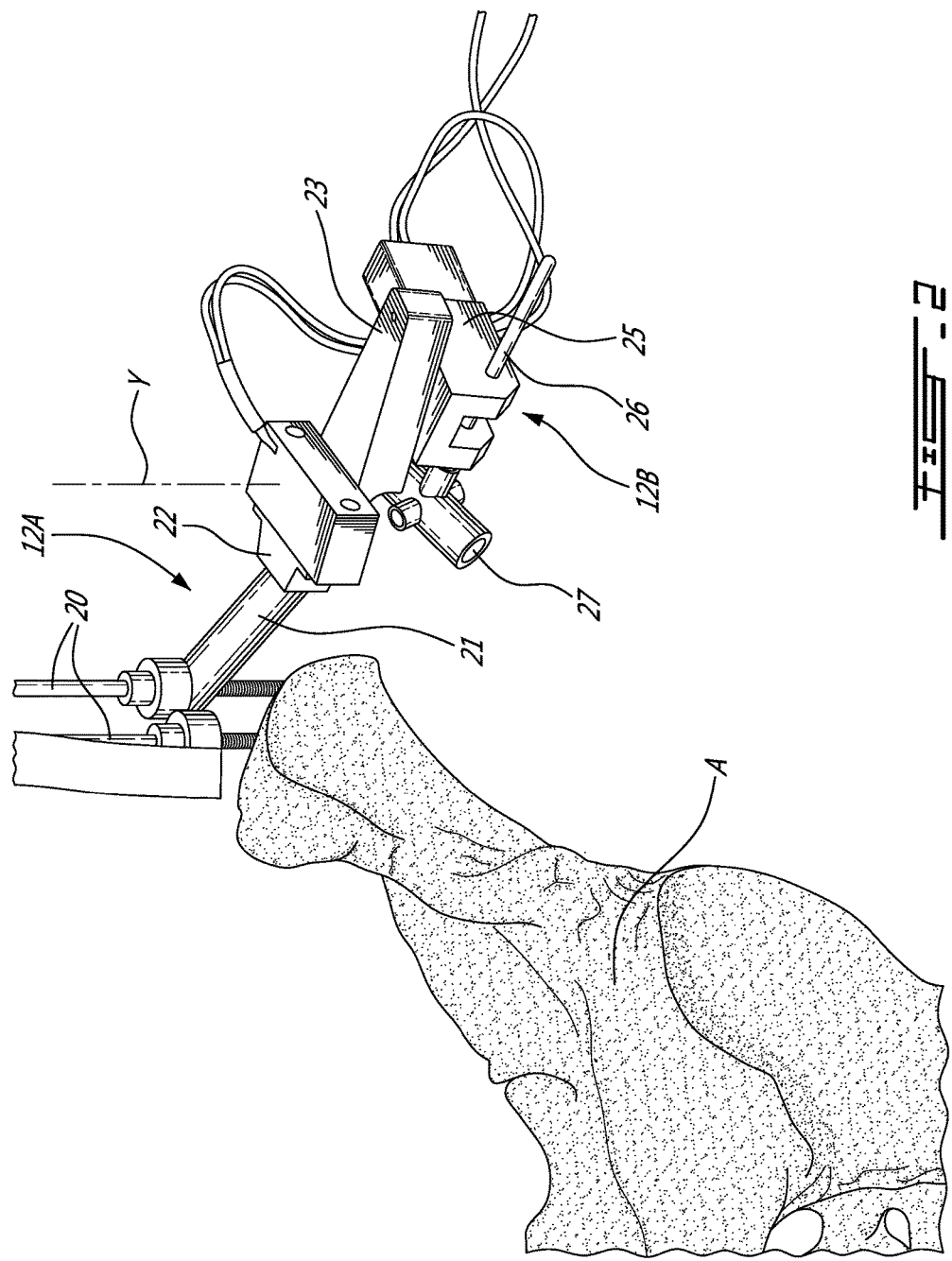
FIG. 2 is a schematic view of a pelvic reference of the magnetometer CAS system of FIG. 1, as secured to a pelvis.

Referring to FIG. 2, an embodiment of the pelvic reference 12 is shown in greater detail. The bone interface 12A may be secured to the pelvis A by way of pins 20. Other means are considered to secure the bone interface 12A to the body, such as noninvasive straps, as well as other types of bolts, screws, etc, or the bone interface 12A may even be adhered to the patient's skin (e.g., patient's back). The bone interface 12A comprises an articulated arm 21 with a lockable pivot joint 22, enabling the rotation of a magnet support 23 relative to the axis generally illustrated as Y in FIG. 2. In an embodiment, the axis Y is parallel to the pins 20.

The magnetic-field generator 12B consists of a motor 25 mounted onto the magnet support 23. The motor 25 causes the rotation of a shaft 26, at the end of which is a magnet 27. Accordingly, by way of the pivot joint 22, an orientation of the magnet 27, and therefore of a plane of the magnetic field created by the rotating magnet 27, may be adjusted as well. Other joints may be provided on the bone interface 12A to orient the plane of the magnetic field as desired, as the articulated arm 21 may be adjustable in orientation relative to the bone mounting device in three degrees of freedom (DOFs). The reference 12 may have a visible indication (i.e., visual display interface) to display how level the accelerometer plane for instance relative to a table, and also a communications link (RF, wired) so that the inertial sensor data may be read by the processor, it the processor is remote.

Moreover, the joints may be equipped with rotary potentiometers to track the rotation of articulated arm 21 or rotation of the magnet support 23 around pivot joint 22, or other rotational joints in the articulated arm 21. It is also considered to provide inertial sensors from the unit 12C on opposite sides of the articulations of the articulated arm 21, to calculate a relative orientation between parts of the arm 21. According to an embodiment, an orientation of the plane of the magnetic field is updated using data produced by the rotary potentiometers. In an embodiment, the processor used in conjunction with the system 10 (e.g., on the bone interface 12A) or in a separate interface unit (e.g., tablet, pc, etc) has sensors and/or potentiometers interconnected or interrelated to receive all necessary data to calculate positions and/or orientations. Moreover, the choice of materials used for the pelvic reference 12 is made in light to minimize interference on the action of the magnet.

The rotating magnet 27 produces an AC magnetic field. According to an embodiment, the motor 25 is a DC motor having magnet 27 installed on a motor shaft. Alternatively, it is considered to use an AC motor without a rotor.

According to an embodiment, the rotating magnet 27 is a spinning cylindrical magnet of a given length. The rotating magnet 27 generates a sinusoidal response in a magnetometer. The reference 12 may have a 2D accelerometer in the inertial sensor unit 12C, with the spinning cylindrical magnet 27 spinning in a plane that is normal to the accelerometer plane. The magnet may spin at a rate of about 200 to 300 RPM, using a small, low-torque, battery powered motor. For instance, a brushed DC motor would be well suited for such application, as it has stationary permanent magnets, so the motor magnets should not generate strong alternating magnetic fields that would interfere with the desired signals. As an alternative, a gear-reduced motor shaft could be used, so that a bandpass filter could remove the noise of the motor, which would be of a higher frequency than the spinning magnet. A motor magnet itself could be used as the signal generator.

Figure 3:
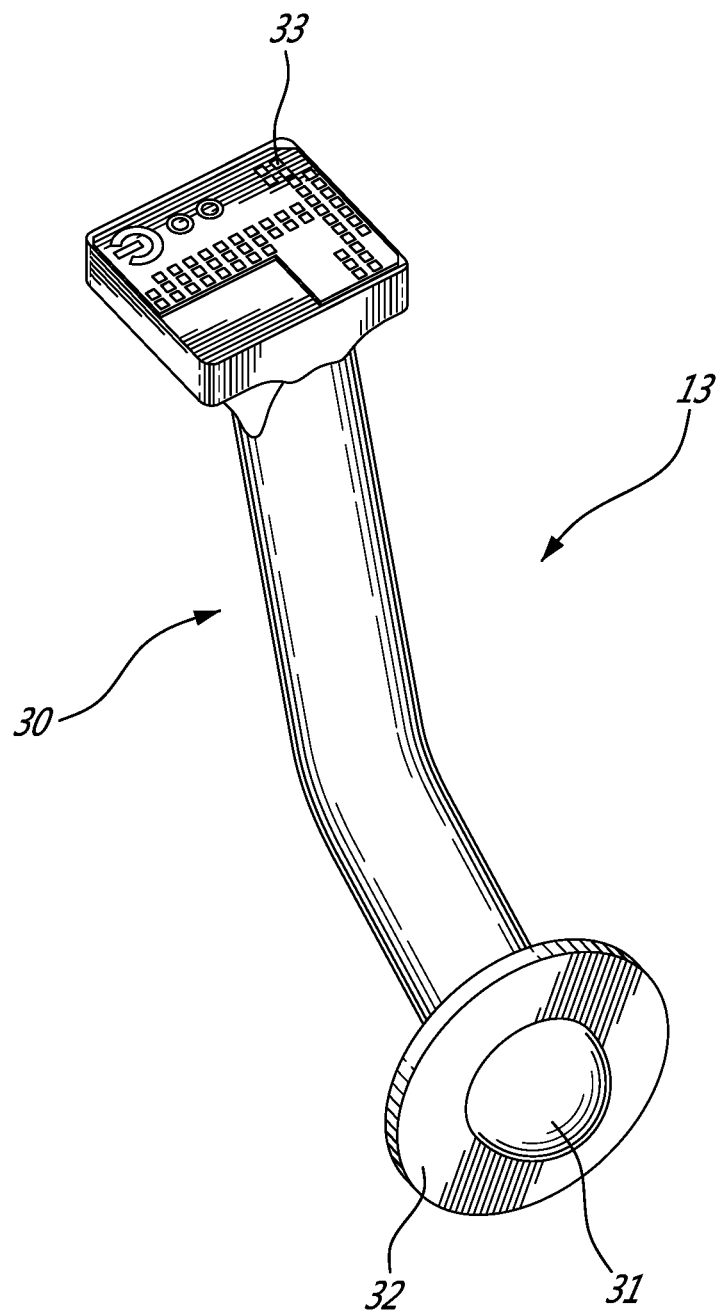
FIG. 3 is a schematic view of an acetabular shell inserter of the magnetometer CAS system of FIG. 1.

Referring to FIG. 3, an example of the surgical tool 13 is illustrated. The tool 13 of FIG. 3 is an acetabular shell validator having a shaft 30 by which the surgical tool 13 may be handled by an operator. The acetabular shell validator 13 is used to determine an orientation of the acetabulum prior to or after being reamed, or to determine the orientation of an acetabular shell implant in the acetabulum. A head 31 is located at a free end of the shaft 30, with a flange 32 delimiting a periphery of the head 31. The head 31 and flange 32 are sized for an acetabular shell (a.k.a., acetabular cup, acetabular or pelvic implant, etc.) to be matingly mounted thereon, with a periphery of the acetabular shell being in abutment with the flange 32. Accordingly, a mating relation between the acetabular shell and the tool 13 is known, and the known mating relation will be used to validate an orientation of the acetabular shell. A magnetometer is inserted into the shaft 30. The magnetometer that is fixed to the instrument 13 may detect AC and DC magnetic fields on three axes.

The AC magnetic field is produced by the rotating magnet 27, while DC magnetic fields produced by the earth or any other mass of metal, such as instruments in the surroundings of the magnetometer, are regarded as noise. By high-pass filtering the response, the static effects of the earth's magnetic field can be removed. Hence, the system 10 is not affected by location on the earth or orientation within a room, and therefore does not require calibration over these effects.

It is known that if a 1-DOF magnetometer is positioned within the spin-plane of a magnet and oriented normal to that plane, the amplitude of the sinusoidal response induced by the magnet will be zero. If the magnetometer is oriented to point directly at the magnet spin center, the amplitude will be a maximum value, and if the magnetometer is oriented to be in the spin plane, but normal to the direction to the spin center, the amplitude will be at a minimum for orientations that are within the spin-plane, and will be relative to the maximum amplitude and the length of the magnet.

Generalizing to out-of-spin-plane positioning of the magnetometer would result in a complex mathematical model. The sensor amplitudes will also become highly variable, due to the $1/(R^3)$ nature of the field strength, as the magnetometer placement along the instrument shaft, away from the rotation center, increases. Given the spherical geometric constraints of travel of the magnetometer on the instrument, however, this is a solvable problem for the desired variables.

Thus, the noise may be removed by an algorithm, while the AC magnetic field is kept for evaluation. The ratio of the amplitude value between X, Y and Z is constant and independent of the varying distance between the magnetometer and the rotating magnet. The ratio is unique for a given angle between the magnetometer and the plane of the rotating magnet. Accordingly, in an embodiment, the arctan of the ratio gives the angle between the magnetometer and the plane of the rotating magnet 27.

In an embodiment, the magnetometer is in alignment with the center of rotation of the head 31 and thus of the acetabular shell when mounted to the head 31. Further electronics include an interface 33 that will provide orientation data (e.g., anteversion, abduction/adduction of shell relative to the pelvis) based on the effect of the magnetic field on the magnetometer within the shaft 30. By knowing the geometric relation between the magnetometer and a working end of the tool 13 (e.g., the head 31 of the validator 30, a shaft of a tool, etc.), an orientation of the working end of the tool 13 may be determined from the readings of the magnetometer regarding the magnetic field produced by the magnetic-field generator 12B of the pelvic reference 12.

The acetabular shell validator is an example among others of a surgical tool that may be used with the CAS system 10. Other tools 13 may be considered as well, as part of the CAS system 10. For instance, spherical reamers, acetabular shell inserters, and other tools from conventional surgical instrument kits could be used as an alternative or in addition to the acetabular shell validator of FIG. 3, and thus be tracked relative to the pelvic reference 12.

Figure 4:
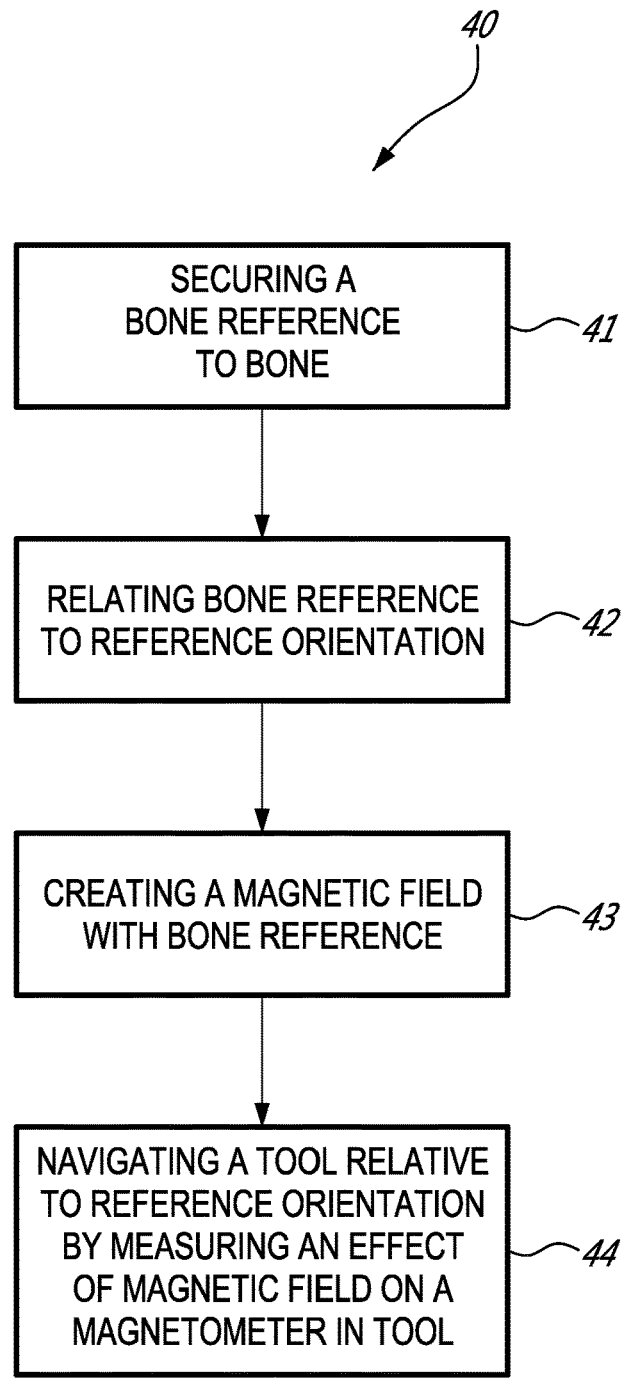
FIG. 4 is a flow chart of a method for navigating tools in CAS using inertial sensors and a rotating magnet.
Figure 5D:
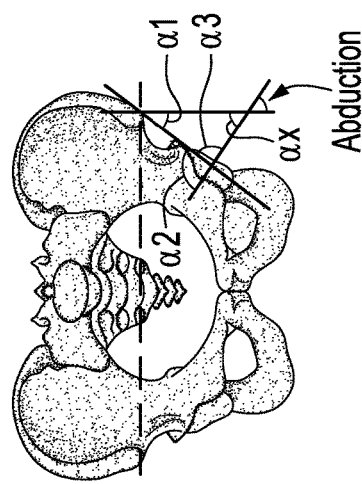
Figure 5C:
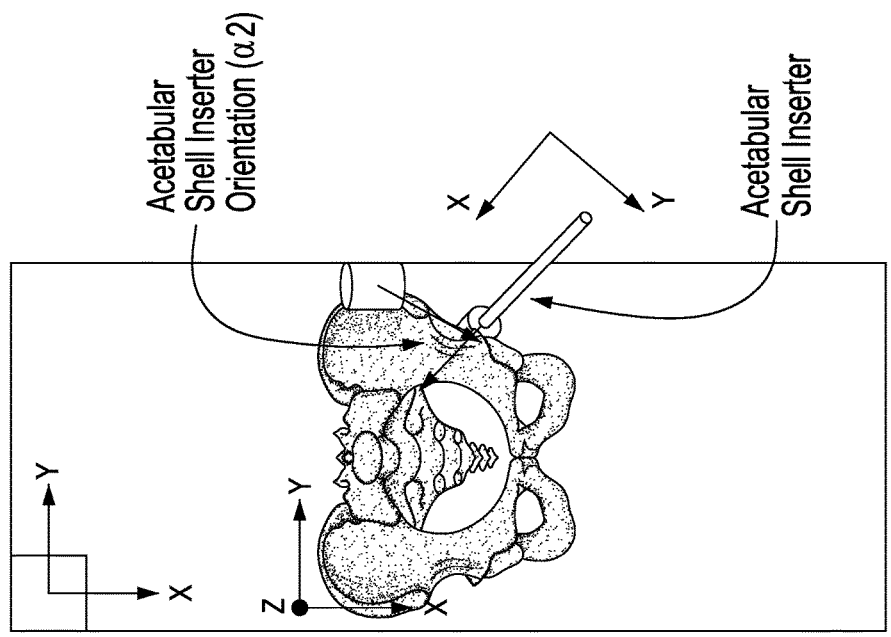

Referring to FIG. 4, a method for the use of the magnetometer CAS system 10 is described and generally shown as 40, for pelvic surgery.

According to 41, with the patient being in a suitable surgery position, the pelvic reference 12 is secured to the bone, or put in a fixed relation relative to the bone, such as the pelvis with the patient positioned in supine decubitus.

According to the illustrated embodiment, the pelvic reference 12 is preferably placed adjacent to the acetabulum that is being operated on. As illustrated in FIG. 2, the pins 20 secure the bone interface 12 on the iliac crest. The technique could also be used with the patient in a lateral decubitus position, among other possibilities.

According to 42, the bone reference 12 is related to the reference orientation using the orientational reference 14. In an embodiment, the reference orientation is a three-axis coordinate system that is created using any appropriate method, and is transferred to the bone reference 12 from the reference orientation 14. It is pointed out that the securing of the bone reference 12 to the pelvis A may be guided by the reference orientation 14.

In an embodiment for pelvic surgery, the reference orientation 14 is defined by the mediolateral axis passing through the anterior superior iliac spines. An anterior-posterior axis of the patient is normal to the plane of the table (when the patient is in supine decubitus), while the longitudinal axis of the patient is a cross-product of the mediolateral axis and the anterior-posterior axis. It is pointed out that the mediolateral axis of the patient may be arranged to be parallel to the plane of the table. In the pelvic embodiment, the inertial sensor unit 12C may be used to calculate the pelvic tilt. For instance, the plane of 2D accelerometers in the inertial sensor unit 12C may be oriented to be normal to the gravity vector prior to dislocation, such that post-dislocation pelvic tilt is measured by the processor of the bone interface 12.

When the rotating magnetic-field plane is parallel to the longitudinal axis of the patient, the plane of the magnetic field defines zero abduction. In some of these instances, the inertial sensor units 12C or like tracking technology may be used to ensure that the orientation of the magnetic field relative to the bone is appropriate.

According to 43, the magnetic field is created by the bone reference 12 by actuation of the motor 25, causing a rotation of the magnet 27. Referring to FIGS. 5A to 5D, according to an embodiment of pelvic surgery, the rotating magnetic-field plane is aligned with the center of rotation of the acetabulum. This may be done by turn the spin plane of the magnet 27 using the joints on the articular arm 21 by the angle between its reference position and the projection line from the new gravity vector to the adjustment plane, plus an angle measured between (1) a line passing through the two anterior superior iliac spines (ASIS), and (2) a line passing through the proximal ASIS and the femoral head center. Another is to turn the spin plane of the magnet 27 until the ratio of the response magnitudes from the strongest responding magnetometer to the weakest responding magnetometer is maximized. The tool 30 should be held relatively still during this measurement. These two measurements will be slightly different, as the center of the tool 30 may not be fully seated until after reaming, at which point the two measurements would be ideally the same. Given this, it may be possible to provide an indication of reaming depth remaining, if the distance between the near ASIS and the femoral head center is measured from the x-ray. This may require a calibration marker in the x-ray. The pelvic reference 12 is preferably provided with suitable tracking, such as a rotary potentiometer, so as to note an abduction angle $\alpha 1$ with the starting point being the zero abduction in which the plane of the rotating magnetic field is parallel to the longitudinal axis of the body.

According to 44, the tool 13 may thus be navigated relative to the reference orientation of the pelvic reference by measuring the effect of the magnetic field on the magnetometer in the tool 13. More specifically, in the embodiment of FIGS. 5A to 5D, the angular rotation between the magnetometer embedded in the tool 13 and the plane of the rotating magnetic field is computed to provide the second part of the abduction angle $\alpha 2$. Accordingly, the abduction angle will be the sum of $\alpha 1 + \alpha 2$. The anteversion may also be obtained as being the angular rotation between inclinometers or like inertial sensors embedded in the instrument 13 and the reference orientation 14.

It is contemplated to use the CAS tracking system to track the displacement of tools relative to bones in other types of orthopedic surgery. In the case of hip replacement, the method 40 is well suited to measure both anteversion and abduction/adduction. When the patient is in supine decubitus, the abduction cannot be measured with inclinometers because the abduction is measured around gravity in this position. Similarly, when the patient is in lateral decubitus, the anteversion cannot be measured with inertial sensors because the anteversion is measured around earth gravity. Therefore, the use of a magnetic field combined with appropriate inclinometers allows both values to be measured.

The invention claimed is:

1. A method for tracking at least one instrument relative to a bone in computer-assisted surgery comprising:
    tracking, using one or more processors of a computer-assisted surgery system, a reference orientation of the bone in three axes with a reference device connected to the bone;
    creating a magnetic field plane by rotating a magnet connected to one of the instrument and the bone;
    using a magnetometer being mounted to the other of the instrument and the bone, producing signals as a function of at least an orientation of the magnetometer relative to the magnetic field plane; and
    tracking and outputting, using one or more processors of a computer-assisted surgery system, an orientation of the instrument relative to the three axes of the reference orientation of the bone using said signals from the magnetometer subjected to the magnetic field plane, as the instrument is moved relative to the bone.

2. The method according to claim 1, wherein the tracking and outputting are performed using the one or more processors in the instrument.

3. The method according to claim 1, wherein creating the magnetic field plane by rotating the magnet connected to one of the instrument and the bone comprises creating the magnetic field plane by rotating the magnet connected to the bone by the reference device.

4. The method according to claim 1, wherein tracking the reference orientation of the bone in three axes with the reference device comprises producing data using at least one of inertial sensors and potentiometers on the reference device.

5. The method according to claim 1, wherein the method is performed on a pelvis, and wherein tracking and outputting the orientation of the instrument comprises tracking and outputting the orientation as the instrument is mated in one of the acetabulum and an acetabular shell.

6. The method according to claim 5, wherein tracking the reference orientation includes tracking one of said axes of the reference orientation as aligned with a mediolateral axis of the pelvis.

7. The method according to claim 1, wherein tracking and outputting the orientation of the instrument comprises displaying navigation data of the instrument relative to the bone.

8. The method according to claim 7, wherein the method is performed on a pelvis, and wherein displaying navigation data of the instrument relative to the bone includes displaying at least one of an anteversion and abduction/adduction of an axis of the instrument relative to the pelvis.

9. The method according to claim 1, wherein the rotating magnet is connected to the bone by an articulated arm, and further comprising sensing an orientation of the rotating magnet relative to the bone to orient the magnetic field plane.

10. The method according to claim 9, wherein sensing the orientation of the rotating magnet relative to the bone to orient the magnetic field plane includes obtaining signals from potentiometers on the articulated arm.

11. The method according to claim 1, further comprising filtering the signals from the magnetometer to remove static effects from earth's magnetic field.

* * * * *